(12) United States Patent
Williams, Sr.

(10) Patent No.: US 9,227,039 B1
(45) Date of Patent: Jan. 5, 2016

(54) HOLDER FOR MEDICAL IV OR CATHETER DEVICE

(71) Applicant: Robert H. Williams, Sr., Waynesville, NC (US)

(72) Inventor: Robert H. Williams, Sr., Waynesville, NC (US)

( * ) Notice: Subject to any disclaimer, the term of this patent is extended or adjusted under 35 U.S.C. 154(b) by 419 days.

(21) Appl. No.: 13/786,816

(22) Filed: Mar. 6, 2013

(51) Int. Cl.
*A61M 5/32* (2006.01)
*A61M 25/02* (2006.01)
*A45F 5/00* (2006.01)

(52) U.S. Cl.
CPC .......... *A61M 25/02* (2013.01); *A45F 2005/008* (2013.01); *A61M 2025/0213* (2013.01); *A61M 2025/0253* (2013.01)

(58) Field of Classification Search
CPC .......... A61M 2025/026; A61M 25/02; A61M 2025/0213; A61M 2025/0206; A61M 2025/0253; A61M 2025/0273; A61M 2025/0266; A61M 39/08; A61M 5/158; A61M 2005/1586; Y10S 128/26; Y10S 128/06; Y10T 24/27; Y10T 24/2708
See application file for complete search history.

(56) References Cited

U.S. PATENT DOCUMENTS

| | | | | |
|---|---|---|---|---|
| 3,677,250 | A | * | 7/1972 | Thomas .......................... 604/180 |
| 4,096,863 | A | * | 6/1978 | Kaplan et al. .................. 604/179 |
| 4,445,894 | A | | 5/1984 | Kovacs |
| 4,470,410 | A | | 9/1984 | Elliott |
| 4,591,356 | A | | 5/1986 | Christie |
| 4,662,873 | A | * | 5/1987 | Lash et al. ..................... 604/179 |
| 4,669,458 | A | | 6/1987 | Abraham et al. |
| 4,799,923 | A | | 1/1989 | Campbell |
| 4,844,061 | A | * | 7/1989 | Carroll ..................... 128/207.17 |
| 4,846,807 | A | | 7/1989 | Safadago |
| 4,870,976 | A | | 10/1989 | Denny |
| 4,898,587 | A | | 2/1990 | Mera |
| 4,966,590 | A | | 10/1990 | Kalt |
| 5,116,324 | A | * | 5/1992 | Brierley et al. ............... 604/180 |
| 5,188,608 | A | | 2/1993 | Fritts |
| 5,292,312 | A | | 3/1994 | Delk et al. |
| 5,549,567 | A | | 8/1996 | Wolman |
| 6,375,639 | B1 | | 4/2002 | Duplessie et al. |
| 7,022,111 | B2 | | 4/2006 | Duplessie et al. |
| 7,793,892 | B1 | | 9/2010 | Bowen et al. |
| 2008/0071224 | A1 | * | 3/2008 | Forsyth ......................... 604/179 |

\* cited by examiner

*Primary Examiner* — Nathan R Price
*Assistant Examiner* — Morgan Lee
(74) *Attorney, Agent, or Firm* — The Van Winkle Law Firm; David M. Carter; William G. Heedy

(57) ABSTRACT

A holder or stabilizing device for medical IV or catheters having flexible tubing attached. An elongated strap-like panel made of a flexible material has an intermediate portion and a pair of attachment portions extending in opposite directions from the intermediate portion, the intermediate and attachment portions defining opposite side edges of the panel. The panel has an outside side generally visible during use. A pair of tubing-securing apertures is provided in the intermediate portion located generally adjacent respective opposite sides of the panel and across from each other, with an adhesive area on the intermediate portion on the outside side between the at least one pair of tubing-securing apertures and is positioned so as to engage the flexible tubing when passing through and extending on the outside side of the panel between the pair of tubing-securing apertures. A set of holders may be provided, color-coded to indicate particular size.

14 Claims, 7 Drawing Sheets

HOLDER FOR MEDICAL IV OR CATHETER DEVICE

BACKGROUND OF THE INVENTION

The invention relates generally to holders or stabilizers for medical IV or catheter devices.

Although there are a number of prior art holders or stabilizers for medical IV or catheter devices having flexible tubing attached, conventional practice nevertheless is to employ tape to hold such devices. Upon removal, uncomfortable pulling of hair can result. In the case of older patients, the tearing of skin can result.

SUMMARY OF THE INVENTION

In one aspect, a holder for a medical IV or catheter device having flexible tubing attached is provided. The holder includes an elongated strap-like panel having an intermediate portion and a pair of attachment portions extending in opposite directions from the intermediate portion and terminating at ends of the panel to define a panel longitudinal axis extending between the ends, the intermediate and attachment portions defining opposite side edges of the panel, and the panel being made of a flexible material and having an outside side generally visible during use and an inside side generally hidden during use. The attachment portions have attachments for securing the panel around a portion of a patient's body, with the outside side visible. At least one pair of tubing-securing apertures is provided in the intermediate portion located generally adjacent respective opposite sides of the panel and across from each other. An adhesive area is provided on the intermediate portion on the outside side between the at least one pair of tubing-securing apertures and is positioned so as to engage the flexible tubing when passing through and extending on the outside side of the panel between the pair of tubing-securing apertures.

In another aspect, a set of holders for a medical IV or catheter device having flexible tubing attached is provided, the holders of the set being of different sizes. Each of the holders includes an elongated strap-like panel having an intermediate portion and a pair of attachment portions extending in opposite directions from the intermediate portion and terminating at ends of the panel to define a panel longitudinal axis extending between the ends, the intermediate and attachment portions defining opposite side edges of the panel, and the panel being made of a flexible material and having an outside side generally visible during use and an inside side generally hidden during use. The attachment portions have attachments for securing the panel around a portion of a patient's body, with the outside side visible. At least one pair of tubing-securing apertures is provided in the intermediate portion located generally adjacent respective opposite sides of the panel and across from each other. An adhesive area is provided on the intermediate portion on the outside side between the at least one pair of tubing-securing apertures and is positioned so as to engage the flexible tubing when passing through and extending on the outside side of the panel between the pair of tubing-securing apertures. The holders of the set of holders are individually color-coded to indicate particular holder size.

In yet another aspect, a holder for a medical IV or catheter device having flexible tubing attached is provided. The holder includes an elongated strap-like panel having an intermediate portion and a pair of attachment portions extending in opposite directions from the intermediate portion and terminating at ends of the panel to define a panel longitudinal axis extending between the ends, the intermediate and attachment portions defining opposite side edges of the panel, and the panel being made of a flexible material and having an outside side generally visible during use and an inside side generally hidden during use. The attachment portions have attachments for securing the panel around a portion of a patient's body, with the outside side visible. An access aperture is provided in the intermediate portion, as well as first and second pairs of tubing-securing apertures. The tubing-securing apertures of each pair are located on opposite sides of the panel and across from each other, the first pair of tubing-securing apertures being located on one panel-end side of the access aperture, and the second pair of tubing-securing apertures being located on the other panel-end side of the access aperture. First and second adhesive areas are provided on the intermediate portion on the outside side between the tubing-securing apertures of each pair, the adhesive areas positioned so as to engage the flexible tubing when passing through and extending on the outside side of panel between a pair of tubing-securing apertures. To aid in positioning, a pair of thumb straps are provide on respective ones of the pair of attachment portions adjacent one of the side edges on the inside side of the panel.

DETAILED DESCRIPTION

Figure 1:
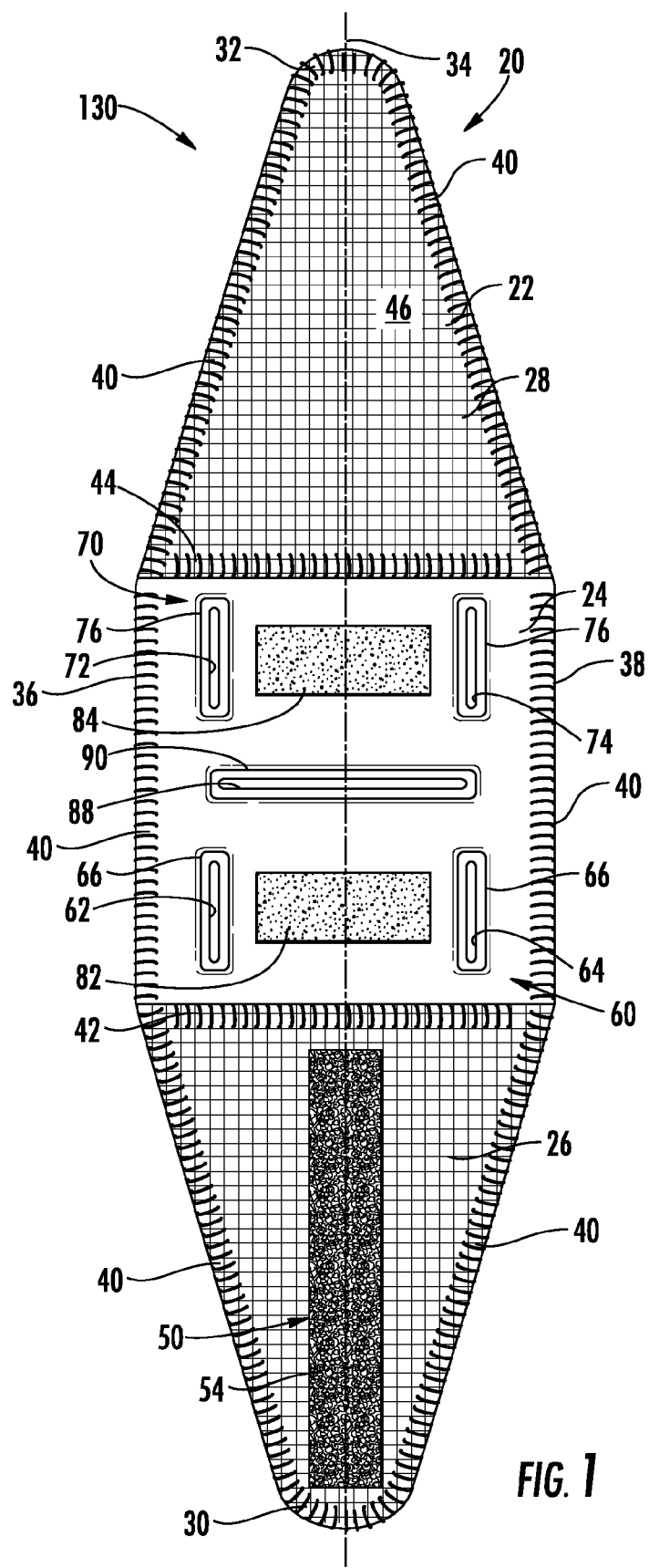
FIG. 1 is a view of the outside side (visible during use) of a flexible fabric holder embodying the invention laid out flat, referred to herein as a "Size 2" holder, and color-coded in part as yellow.
Figure 2:
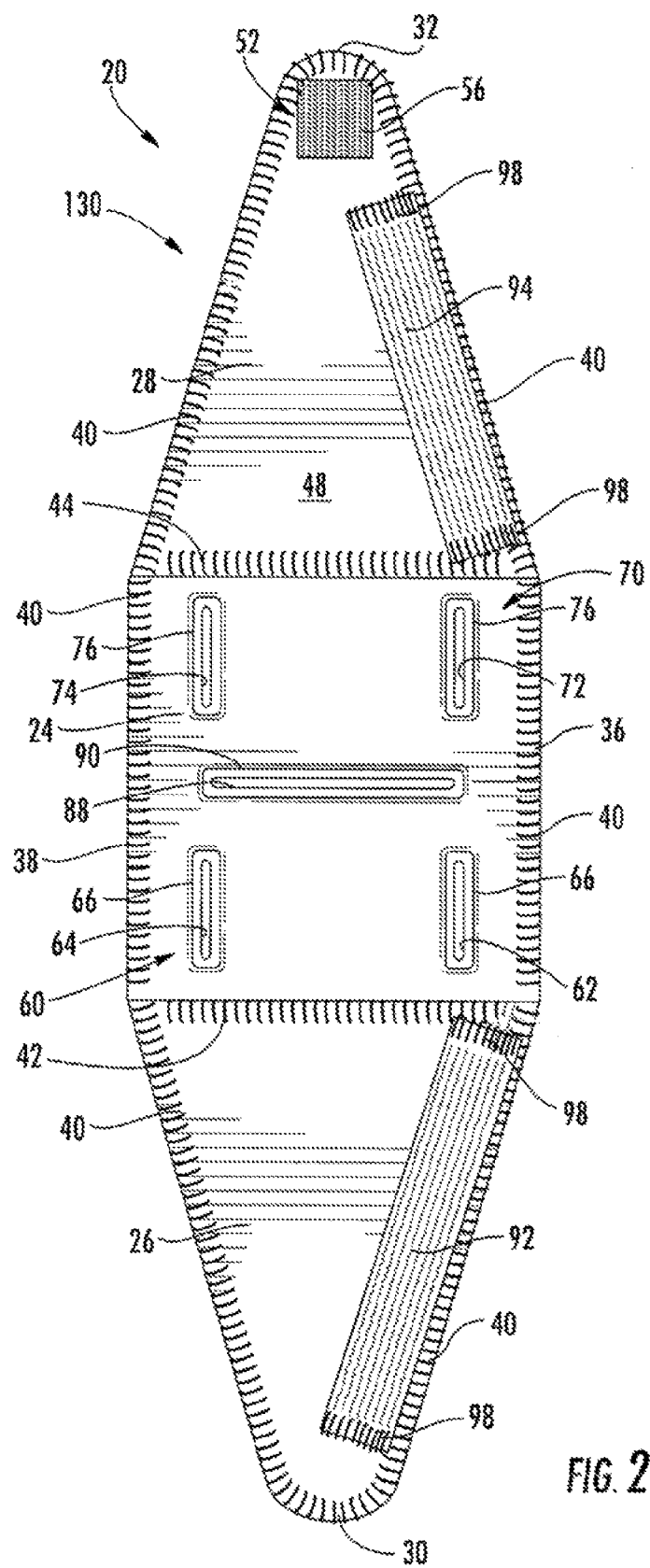
FIG. 2 is a view of the inside side (generally hidden during use) of the holder of FIG. 1, the holder in FIG. 2 being turned over with reference to FIG. 1.

Referring first to FIGS. 1 and 2, a holder 20 embodying the invention takes the general form of an elongated strap-like panel 22, generally made of flexible fabric material. The holder includes an intermediate portion 24 and a pair of attachment portions 26 and 28 extending in opposite directions from the intermediate portion 24. The attachment portions 26 and 28 terminate at respective ends 30 and 32. A longitudinal axis 34 is defined by and extends between the ends 30 and 32. In addition, the intermediate 24 and attachment 26 and 28 portions define opposite side edges 36 and 38 of the panel 22.

In the illustrated embodiment the intermediate portion 24 is rectangular, essentially square, and the attachment portions 26 and 28 are generally triangular, but with rounded vertices at the ends 30 and 32. It will however be appreciated that the elongated strap-like panel 22, in particular the portions 24, 26 and 28, may have other configurations.

As noted above, the strap-like panel 22 is made of a flexible material, typically fabric. The panel 22 may include two (or more) fabric layers. The intermediate portion 24 in particular may include additional intermediate layers of padding material. Peripheral stitching 40 secures the layers together, and intermediate transverse stitching 42 and 44 secures the layers of the intermediate portion 24.

The panel 22 has an outside side 46, shown in FIG. 1, and an inside side 48, shown in FIG. 2. The outside side 46 of FIG. 1 is generally visible during use, and the inside side 48 of FIG. 2 is generally hidden during use.

As also depicted in FIG. 1, the holder 20 is color-coded to indicate a particular holder size. In the illustrated embodiment, the attachment portions 26 and 28 are color-coded on the outside side 46, hatched to represent yellow in the illustrated embodiment. The intermediate portion 24 is not color-coded in the illustrated embodiment, nor is the inside side 48.

An important aspect of the holder 20 embodying the invention is comfort to a patient. Upon removal, the pulling of hair is generally avoided, as well as the tearing of skin of older patients.

For securing the strap-like panel 22 around a portion of a patient's body, the attachment portions 26 and 28 include attachments generally designated 50 and 52, respectively. Presently preferred are hook-and-loop fastener elements. Even so, other suitable attachments may be employed, such as, by way of example and not limitation, buttons, snaps, and string ties.

In the illustrated embodiment, the attachment 50, as the first element of a hook-and-loop fastener, more particularly takes the form of a strip 54 of "loop" material, visible in FIG. 1, on the outside side 46 of the panel 22, and more particularly on the attachment portion 26, extending generally along the longitudinal axis 34.

As the second element of a hook-and-loop fastener, the attachment 52, visible in FIG. 2, takes the form of a square piece 56 of "hook" material on the inside side 48 of the panel 22, on the attachment portion 28 near the panel end 32.

It will be appreciated that the illustrated attachments 50 and 52 are adjustable to fit different size body parts.

Formed in the intermediate portion 24 is at least one pair 60 of tubing-securing apertures 62 and 64 generally adjacent respective opposite sides 36 and 38 of the panel 22, and across from each other. In other words, a line between the tubing-securing apertures 62 and 64 is generally perpendicular to the longitudinal axis 34. The tubing-securing apertures 62 and 64 are slotted, generally of "buttonhole" configuration, and extend generally parallel to the longitudinal axis 34. The "buttonhole" configuration is characterized by peripheral stitching 66.

In the illustrated embodiment, the pair 60 of tubing-securing apertures 60 is a first pair 60 of tubing-securing apertures. In addition, there is a second pair 70 of tubing-securing apertures 72 and 74, likewise located generally adjacent respective opposite sides 36 and 38 of the panel 22, and across from each other. The tubing-securing apertures 72 and 74 of the second pair 70 also are slotted and extend generally perpendicular to the longitudinal axis 34, and have peripheral buttonhole stitching 76.

For selectively engaging flexible tubing 80 (FIGS. 3 and 4), the holder 20 of FIGS. 1 and 2 includes, on the intermediate portion 24 between the first pair 60 of tubing-securing apertures 62 and 64, and between the second pair 70 of tubing-securing apertures 72 and 74, respective adhesive areas 82 and 84. The adhesive areas 82 and 84 are positioned so as to engage the flexible tubing 80 when passing through and extending on the outside side 46 of the panel 22 between either the first pair 60 of tubing-securing apertures 62 and 64, or the second pair 70 of tubing-securing apertures 72 and 74, whichever happens to be in use. Preferably, the adhesive areas 82 and 84 take the form of double-sided adhesive tape, with removable peel-off strips protecting the adhesive areas 82 and 84 prior to use, and when not in use.

Also formed in the intermediate portion 22 of the holder 20 is an access aperture 88. The access aperture is slotted, in the manner of an elongated "buttonhole", and extends generally perpendicular to the longitudinal axis 34. The access aperture 88 includes conventional buttonhole peripheral stitching 90.

To aid in positioning, the holder 20 additionally includes, on the inside side 48 of the panel 22, visible in FIG. 2, a pair of thumb straps 92 and 94, which may be made of an elastic strap material, on respective sides 26 and 28 of the pair of attachment portions 26 and 28, adjacent one of the side edges 36 or 38, in the illustrated embodiment side edge 36, on the inside side 48 of the panel 22. The thumb straps 92 and 94 are secured at their ends by stitching 98. Two thumb straps 92 and 94 are provided, in a symmetrical arrangement, although only one at a time is used, depending on the orientation of the holder 20 and the hand of the person applying.

Figure 3:
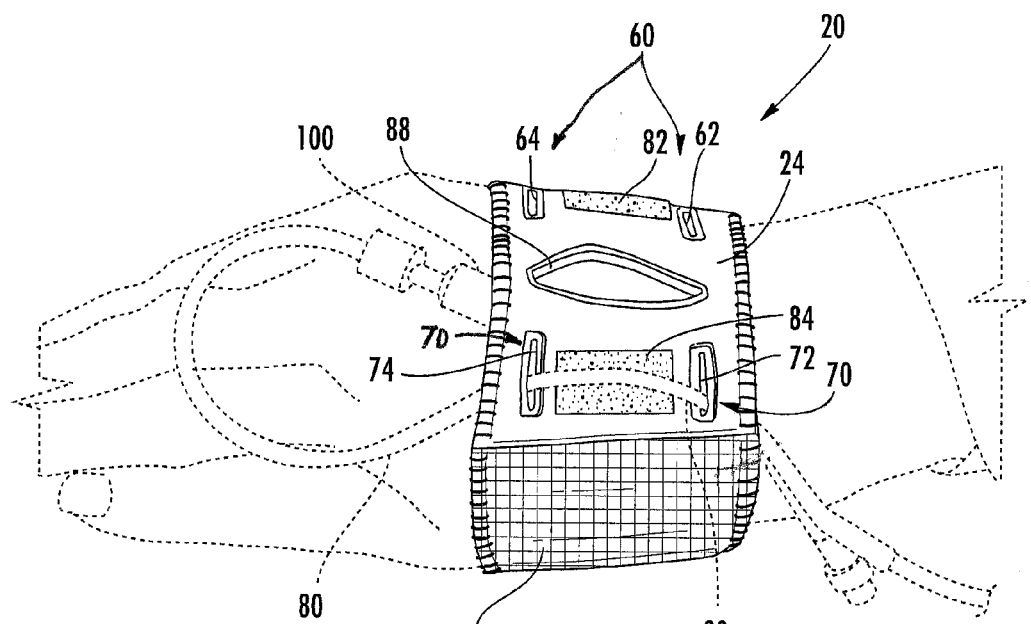
FIG. 3 illustrates the holder of FIGS. 1 and 2 in use securing a medical IV or catheter device attached near the wrist of a patient.

Referring now to FIG. 3, the holder 20 of FIGS. 1 and 2 is shown in use, for example on the top of the hand of a patient, with a medical IV or catheter device 100 inserted near the wrist of a patient. The medical IV or catheter device 100 is conventional, and may take any one of a variety of forms. The flexible tubing 80 is attached to the medical IV or catheter device 100.

During use, a nurse, for example, inserts the medical IV or catheter device 100, and may optionally employ a small piece of tape (not shown) to hold the device 100 in place temporarily. The elongated strap-like panel 22 is then wrapped around the patient's hand as illustrated, and secured employing the attachments 50 and 52. The thumb strap 92 or 94 may be engaged and used as an aid in positioning. In the particular example of FIG. 3, the flexible tubing 80 is looped through the second pair 70 of tubing-securing apertures 72 and 74 and engaged by the adhesive area 84. The flexible tubing 80 may be looped through the buttonholes 72 and 74 either before or after the holder 20 is applied. The access aperture 88 provides access to the medical IV or catheter device 100.

Figure 4:
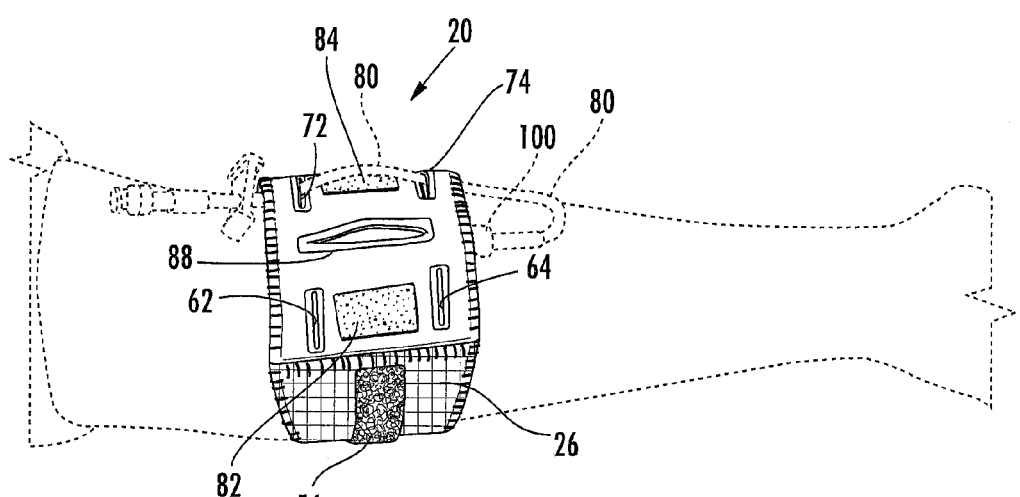
FIG. 4 similarly illustrates the holder of FIGS. 1 and 2 in use attached near the elbow of a patient.

FIG. 4 similarly illustrates the holder 20 of FIGS. 1 and 2 attached as another example to the arm of a patient, near the elbow.

Figure 5:
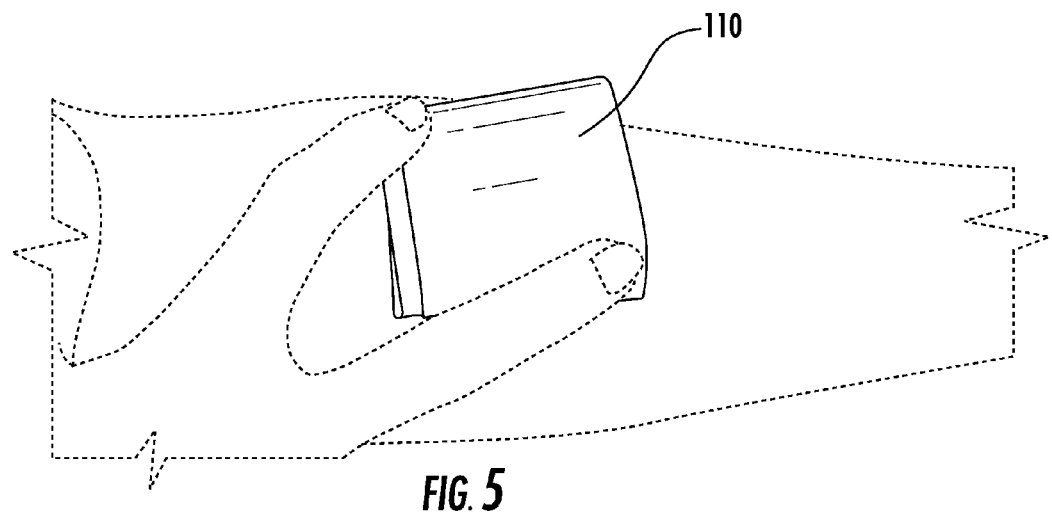
FIG. 5 illustrates an initial step in alternatively employing the holder of FIGS. 1 and 2 as a bandage holder.
Figure 6:
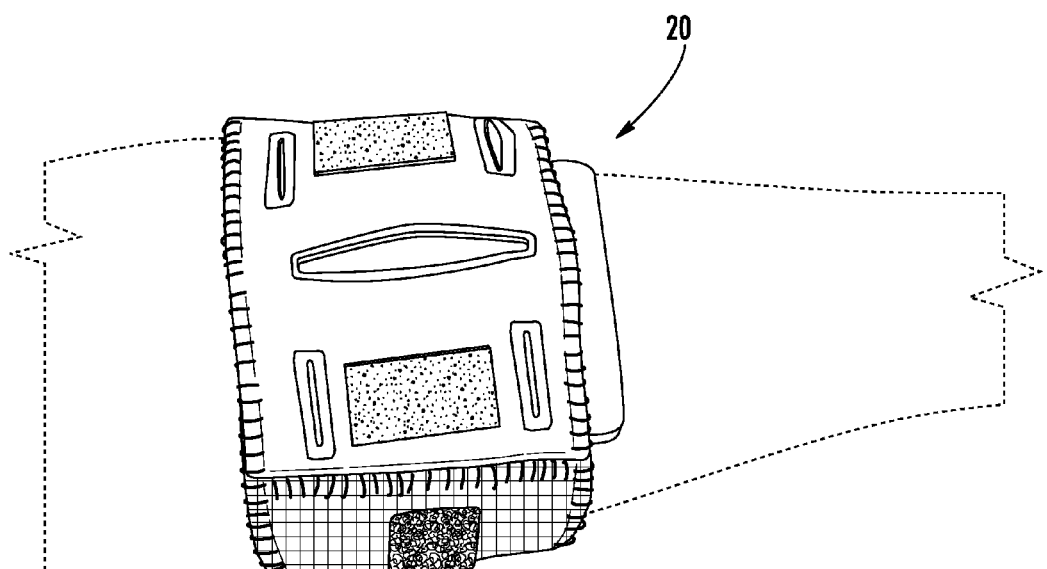
FIG. 6 depicts a subsequent step in alternatively employing the holder of FIGS. 1 and 2 as a bandage holder.

FIGS. 5 and 6 illustrate an alternative use of the holder 20, as a bandage holder. To use as a bandage holder, and referring in particular to FIG. 5, a piece of gauze 110 is placed over a wound, and then secured in place by wrapping the holder 20 around, and securing employing the attachments 50 and 52.

Figure 7:
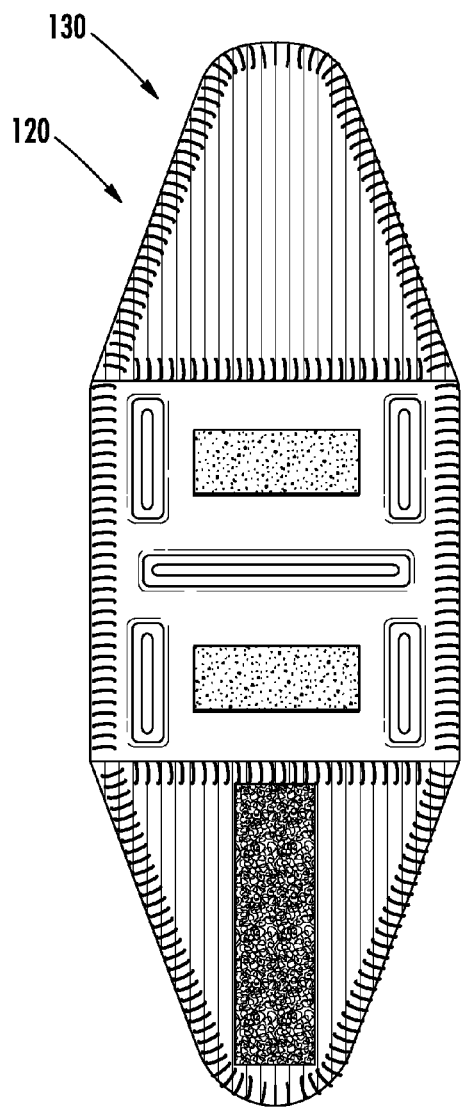
FIG. 7 is a view of the outside side of another holder embodying the invention, referred to herein as a "Size 1" holder, and color-coded in part as red.
Figure 8:
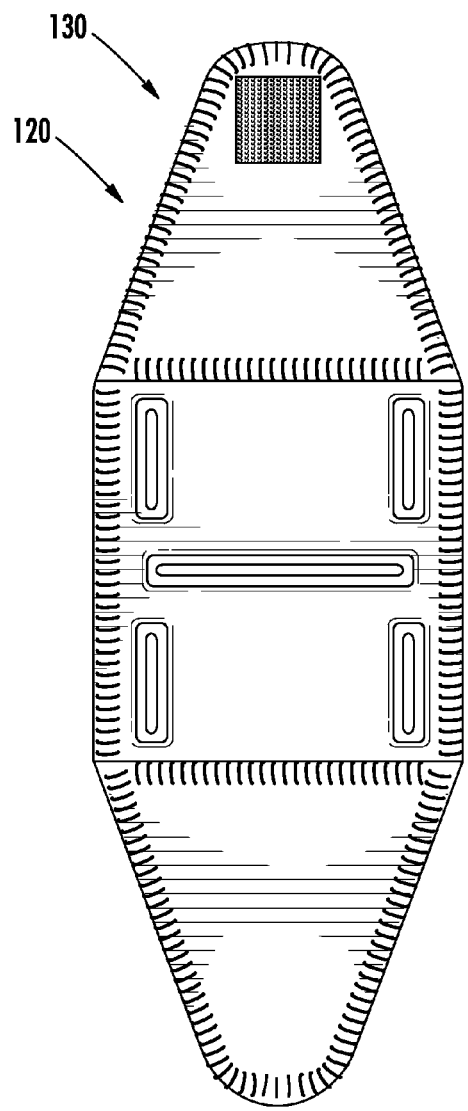
FIG. 8 shows the inside side of the "Size 1" holder of FIG. 7.
Figure 9:
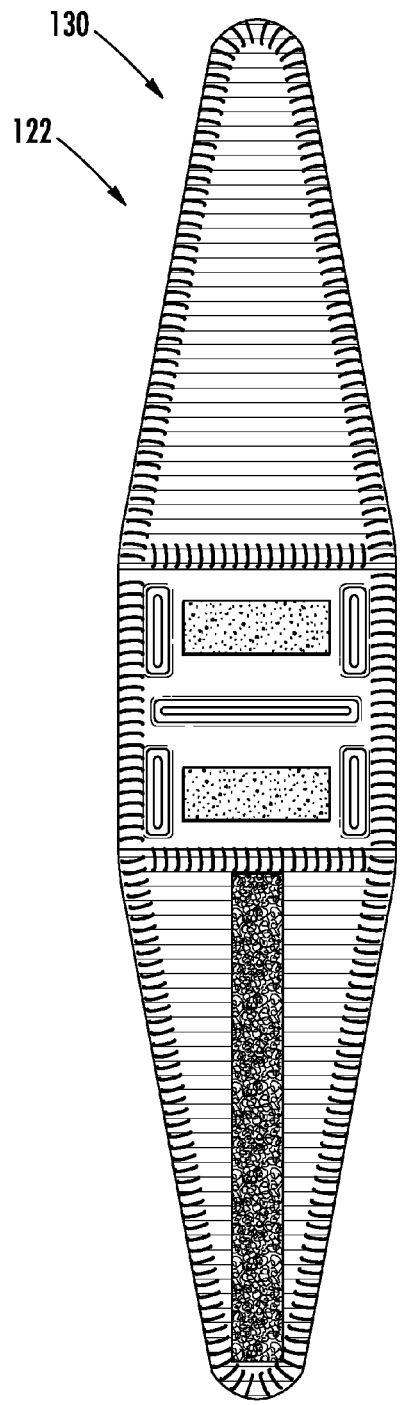
FIG. 9 is a view of the outside side of yet another holder embodying the invention, referred to herein as a "Size 3" holder, and color-coded in part as blue.
Figure 10:
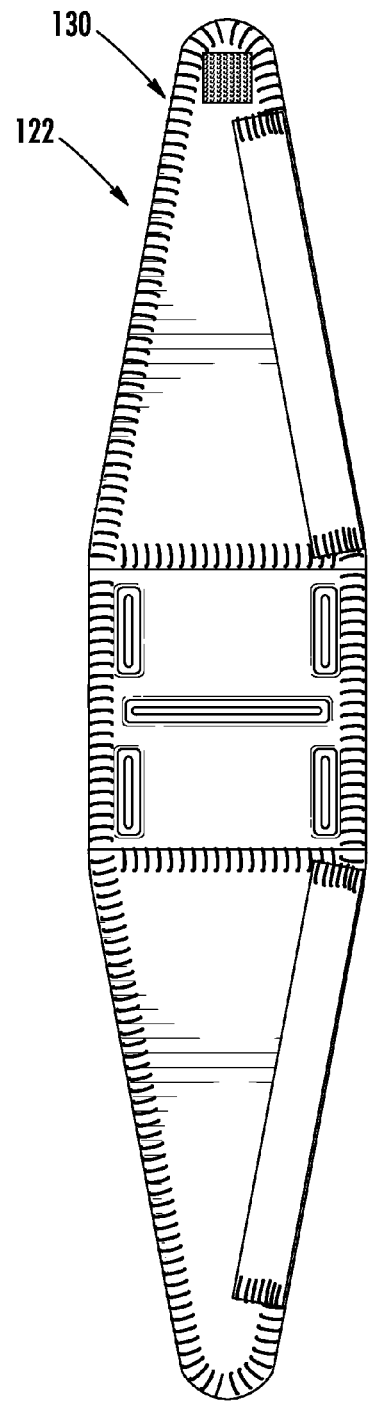
FIG. 10 shows the inside side of the "Size 3" holder of FIG. 9.
Figure 11:
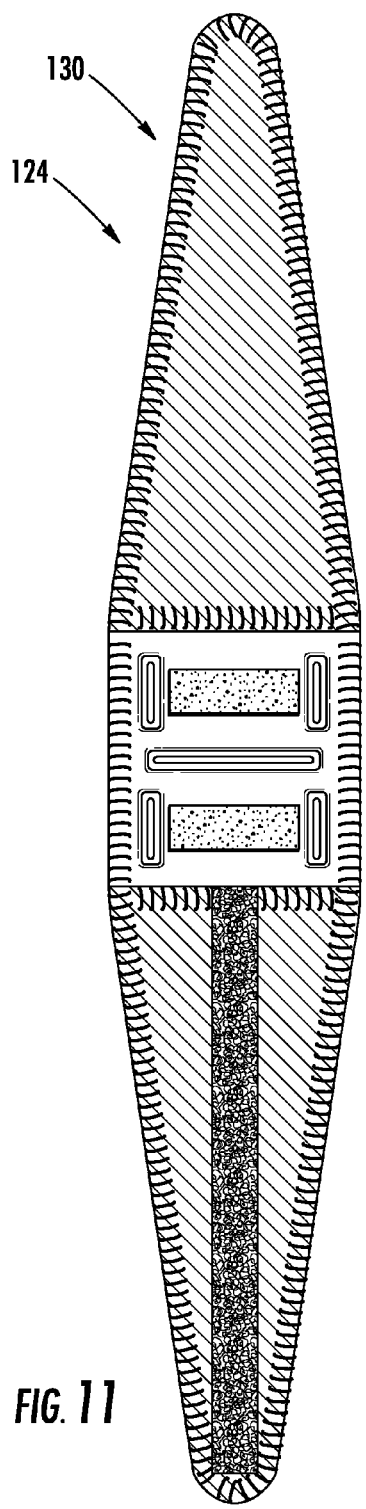
FIG. 11 is a view of the outside side of still another holder embodying the invention, referred to herein as a "Size 4" holder, and color-coded in part as green.
Figure 12:
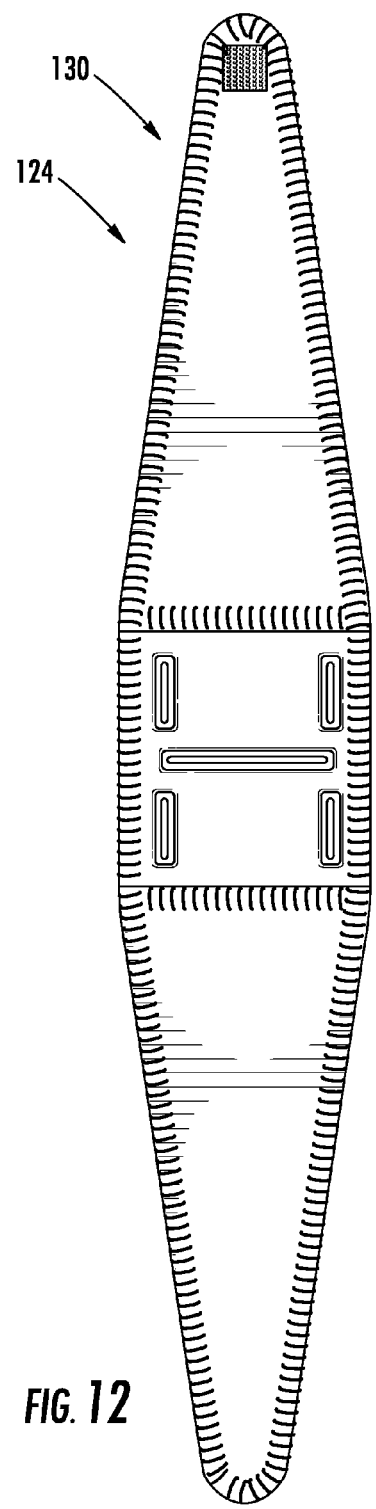
FIG. 12 shows the inside side of the "Size 4" holder of FIG. 11.

To fit different sizes of individuals (for example, from infants through adults, and additionally to fit different body parts) a set of holders embodying the invention may be provided in different holder sizes, individually color-coded to indicate particular holder size. Thus, the "Size 2" holder of FIGS. 1 and 2 (color-coded for yellow), a "Size 1" holder 120 of FIGS. 7 and 8 (color-coded for red), a "Size 3" holder 122 (color-coded for blue) and a "Size 4" holder 124 (color-coded for green) in FIGS. 11 and 12 together constitute a set 130 of holders. The holders 120, 122 and 124 of FIGS. 7, 8, FIGS. 9, 10 and FIGS. 11, 12 function in the same manner as the holder 20 described above, and are employed depending on the particular size required. The different overall sizing of the holders 20, 120, 122 and 124 is in addition to the smaller adjustment range provided by the attachments 50 and 52.

Each of the holders 20, 120, 122 and 124 is approximately two and three-fourths inches in width, between the side edges 36 and 38 at the intermediate portion 24. Also, the intermediate portion 24 of each holder is approximately two and three-fourths inches square. The individual holders, however, differ in length. The "Size 1" holder 120 of FIGS. 7 and 8, color-coded red, is approximately six and one-half inches between the panel ends 30 and 32. The "Size 2" holder of FIGS. 1 and 2, color-coded yellow, is approximately ten inches from end 30 to end 32. The "Size 3" holder 122 of FIGS. 9 and 10, color-coded blue, is approximately twelve inches from end 30 to end 32. The "Size 4" holder 124 of FIGS. 11 and 12, color-coded green, is approximately seventeen inches from end 30 to end 32.

While specific embodiments of the invention have been illustrated and described herein, it is realized that numerous modifications and changes will occur to those skilled in the art. It is therefore to be understood that the appended claims are intended to cover all such modifications and changes as fall within the true spirit and scope of the invention.

What is claimed is:

1. A holder for a medical IV or catheter device having flexible tubing attached, said holder comprising:
    an elongated strap-like panel having an intermediate portion and a pair of attachment portions extending in opposite directions from said intermediate portion and terminating at ends of said panel to define a panel longitudinal axis extending between said ends, said intermediate and attachment portions defining opposite side edges of said panel, and said panel being made of a flexible material and having an outside side generally visible during use and an inside side generally hidden during use;
    said attachment portions having attachments for securing said panel around a portion of a patient's body, with said outside side visible;
    at least one pair of tubing-securing apertures in said intermediate portion located generally adjacent respective opposite sides of said panel and across from each other;
    an adhesive area on said intermediate portion on said outside side between said at least one pair of tubing-securing apertures positioned so as to engage the flexible tubing when passing through and extending on said outside side of said panel between said at least one pair of tubing-securing apertures; and
    to aid in positioning, a pair of thumb straps on respective sides of said pair of attachment portions adjacent one of said side edges on said inside side of said panel.

2. The holder of claim 1, wherein said tubing-securing apertures are slotted and extend generally parallel to the longitudinal axis.

3. The holder of claim 1, which further comprises an access aperture in said intermediate portion.

4. The holder of claim 3, wherein said access aperture is slotted and extends generally perpendicular to the longitudinal axis.

5. The holder of claim 1, wherein said adhesive area comprises double-sided adhesive tape.

6. The holder of claim 1, which further comprises:
    another pair of tubing-securing apertures in said intermediate portion located generally adjacent respective opposite sides of said panel and across from each other; and
    another adhesive area on said intermediate portion on said outside side between said another pair of tubing-securing apertures positioned so as to engage the flexible tubing when passing through and extending on said outside side of said panel between said another pair of tubing-securing apertures.

7. The holder of claim 6, wherein said another pair of tubing-securing apertures are slotted and extend generally parallel to the longitudinal axis.

8. The holder of claim 6, which further comprises an access aperture in said intermediate portion located between said adhesive areas.

9. The holder of claim 8, wherein said access aperture is slotted and extends generally perpendicular to the longitudinal axis.

10. The holder of claim 1, wherein said attachments comprise:
    a first element of a hook-and-loop fastener on one of said attachment portions on one of said outside and inside sides of said panel; and
    a second element of a hook-and-loop fastener on the other of said attachment portions on the opposite one of said outside and inside sides of said panel.

11. A holder for a medical IV or catheter device having flexible tubing attached, said holder comprising:
    an elongated strap-like panel having an intermediate portion and a pair of attachment portions extending in opposite directions from said intermediate portion and terminating at ends of said panel to define a panel longitudinal axis extending between said ends, said intermediate and attachment portions defining opposite side edges of said panel, and said panel being made of a flexible material and having an outside side generally visible during use and an inside side generally hidden during use;
    said attachment portions having attachments for securing said panel around a portion of a patient's body, with said outside side visible;
    an access aperture in said intermediate portion;
    first and second pairs of tubing-securing apertures in said intermediate portion, said tubing-securing apertures of each pair being located on opposite sides of said panel and across from each other, said first pair of tubing-securing apertures being located on one panel-end side of said access aperture, and said second pair of tubing-securing apertures being located on the other panel-end side of said access aperture;
    first and second adhesive areas on said intermediate portion on said outside side between said tubing-securing apertures of each pair, said adhesive areas positioned so as to engage the flexible tubing when passing through and extending on said outside side of panel between a pair of tubing-securing apertures; and
    to aid in positioning, a pair of thumb straps on respective sides of said pair of attachment portions adjacent one of said side edges on said inside side of said panel.

12. The holder of claim 11 wherein:
    said first and second pairs of tubing-securing apertures are slotted and extend generally parallel to the longitudinal axis; and wherein
    said access aperture is slotted and extends generally perpendicular to the longitudinal axis.

13. The holder of claim 11, wherein said adhesive areas comprise double-sided adhesive tape.

14. The holder of claim 11, which is color-coded to indicate size.

* * * * *